United States Patent [19]

Boyle

[11] 4,127,660

[45] Nov. 28, 1978

[54] THIAZOLINE DERIVATIVES

[75] Inventor: John T. A. Boyle, Maidenhead, England

[73] Assignee: John Wyeth & Brother Limited, Maidenhead, England

[21] Appl. No.: 861,325

[22] Filed: Dec. 16, 1977

[30] Foreign Application Priority Data

Dec. 22, 1976 [GB] United Kingdom ............... 53492/76

[51] Int. Cl.² .................... C07D 513/04; A61K 31/38
[52] U.S. Cl. ..................................... 424/249; 544/219
[58] Field of Search ......................... 544/219; 424/249

[56] References Cited

PUBLICATIONS

Trepanier et al., *J. of Heterocyclic Chem.*, vol. 7, pp. 1231–1235 (1970).
Trepanier et al., *J. of Heterocyclic Chem.*, vol. 8, pp. 621–627 (1971).

*Primary Examiner*—John M. Ford
*Attorney, Agent, or Firm*—Arthur E. Wilfond

[57] ABSTRACT

New thiazolotriazines having the formula

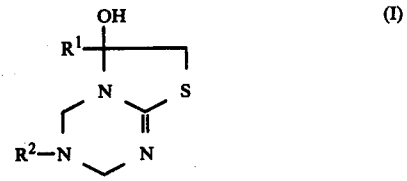

(where $R^1$ is aryl and $R^2$ is ar(lower)alkyl, lower alkyl or lower alkenyl) and their pharmaceutically acceptable acid addition salts are described. The corresponding thiazolotriazinium compounds comprising a cation having the formula

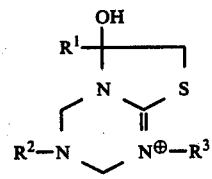

(where $R^1$ and $R^2$ are as explained above and $R^3$ is ar(lower)alkyl, lower alkyl or lower alkenyl) and a pharmaceutically acceptable anion are also described. The compounds are indicated for use as anti-ulcer agents.

12 Claims, No Drawings

THIAZOLINE DERIVATIVES

The present invention concerns novel heterocyclic compounds. In particular the invention provides new thiazolotriazine derivatives and thiazolotriazinium compounds, a process for their preparation and pharmaceutical compositions containing them.

The invention provides novel compounds having the formula I

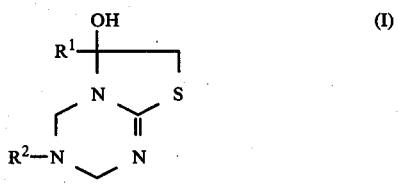

their pharmaceutically acceptable acid addition salts and their derivatives comprising a cation having the formula II

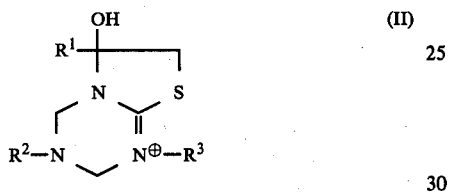

and a pharmaceutically acceptable anion. In formulae I and II $R^1$ represents aryl and $R^2$ represents ar(lower)alkyl, lower alkyl or lower alkenyl. In formula II $R^3$ represents ar(lower)alkyl, lower alkyl or lower alkenyl.

More specifically, $R^1$ may be selected from phenyl and phenyl substituted by one to two substituents selected from halogen, trifluoromethyl, lower alkoxy, lower alkyl, nitro, amino, mono(lower alkyl)amino and di(lower alkyl)amino, $R^2$ may be selected from phen(-lower)alkyl, lower alkyl and lower alkenyl and $R^3$ may be selected from phen(lower)alkyl, lower alkyl and lower alkenyl.

The aryl group denoted by $R^1$ may be, for example, unsubstituted phenyl or phenyl substituted by one or more substituents. As substituents there may be mentioned, halogen, for instance, chlorine or bromine; trifluoromethyl; lower alkoxy, for instance, methoxy, ethoxy, propoxy or butoxy; lower alkyl, for instance, methyl, ethyl, propyl or butyl; nitro; and amino or substituted amino, for instance, mono (lower) alkylamino, for example, methylamino or ethylamino or di(lower alkyl)amino, for example, dimethylamino, ethylmethylamino or diethylamino. $R^2$ represents an ar(lower-)alkyl group, that is an aralkyl group whose alkyl moiety is lower alkyl, preferably phen(lower)alkyl, for instance, benzyl or phenethyl, a lower alkyl group, for instance, methyl, ethyl, propyl or butyl, or lower alkenyl, for instance, allyl, but-2-enyl, 2-methylbut-2-enyl, 3-methylbut-2-enyl or pent-2-enyl. $R^3$, where present, represents ar(lower)alkyl, preferably, phen(lower)alkyl, for example, benzyl or phenethyl, lower alkyl, for instance, methyl, ethyl, propyl or butyl, or lower alkenyl, for instance, allyl, but-2-enyl, 2-methylbut-2-enyl, 3-methylbut-2-enyl or pent-2-enyl. $R^3$ preferably represents lower alkyl, advantageously methyl or ethyl.

The term "lower" as used herein in connection with alkyl and alkoxy groups means that the group contains up to 6 carbon atoms, preferably up to 4 carbon atoms.

The term "lower alkenyl" as used herein means a univalent radical derived by removal of a hydrogen atom from a saturated carbon atom of an ethylenically unsaturated aliphatic hydrocarbon of 3 to 6 carbon atoms, preferably 3 to 4 carbon atoms.

It will be appreciated that the carbon atom at the 6-position in formulae I and II, that is the carbon atom bearing the aryl group $R^1$, is asymmetric and thus the compounds of the invention possess the property of optical isomerism. The invention includes the optical isomers as well as their racemic mixtures. Mixtures of optical isomers may be resolved in known manner.

Although the positive charge of the ion of formula II is illustrated on the nitrogen atom at the 1-position, it will be appreciated by those skilled in the art that the charge is believed to be delocalised between the 1-position and the 5-position. Thus the ion may equally well be illustrated by means of the formula IIa

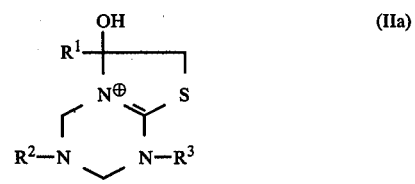

The compounds having formula I, their pharmaceutically acceptable acid addition salts and their derivatives containing the cation of formula II may be prepared by a process wherein a compound having the formula $R^1COCH_2Y$ (wherein $R^1$ is as defined above and Y is a replaceable atom or group, for example, a bromine atom or an organosulphonyloxy group, for instance, p-toluenesulphonyloxy) is reacted with a triazine derivative having the formula

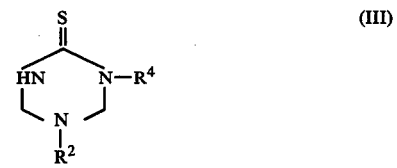

(where $R^2$ is as defined above and $R^4$ is hydrogen or the same as $R^3$). When $R^4$ is hydrogen the reaction product is generally the compound having the formula I in the form of its acid addition salt with the acid HY. If desired, the acid addition salt may be neutralised to yield the compound having formula I in the form of the free base. Other acid addition salts may be formed by treatment of the free base with an acid. When $R^4$ is the same as $R^3$, the product obtained is a thiazolotriazinium compound containing the ion of formula II.

Amongst the new compounds provided by the invention are those of formula I where $R^1$ is aryl and $R^2$ is phen(lower)alkyl or lower alkyl and their pharmaceutically acceptable acid addition salts. They may be obtained by the aforesaid process by using a compound having the formula

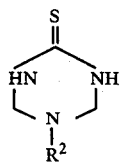

(IV)

where R[2] is phen(lower)alkyl or lower alkyl.

The starting materials of formula $R^1COCH_2Y$ are known compounds or may be prepared in known manner. The triazine derivatives of formula III are known in some cases and, in the other cases, may be prepared in known manner. A literature reference relating to the preparation of the triazine derivatives is Journal of American Chemical Society, 69, 2136 (1947).

We prefer to carry out the process of the invention by using starting materials of formula $R^1COCH_2Y$ where Y is a bromine atom. The aracylbromide may be reacted with the triazine derivative of formula III in solution in a suitable organic solvent, for instance, acetone. Normally this reaction proceeds at ambient laboratory temperature and therefore no heating is generally necessary. We have found it convenient to carry out the process by mixing a solution of the aracylbromide in acetone and a solution of the triazine derivative in acetone and allowing the thiazolotriazine derivative product to separate out from the solution.

The compounds of formula I in the form of the free base may be prepared by neutralisation of an acid addition salt in known manner. The free base may be converted to an acid addition salt by addition of an acid. For example, the hydrochloride may be prepared by treatment with ethereal hydrogen chloride.

The acid addition salts of the compound having formula I include these formed from inorganic acids such as the sulphate, hydrochloride, hydrobromide, hydroiodide, nitrate, phosphate, and organic acids, for example, sulphonates (such as the methane-sulphonate and p-toluenesulphonate), acetate, maleate, fumarate, tartrate and formate.

The thiazolothiazinium compounds of the invention comprise the cation of formula II and a pharmaceutically acceptable anion. The anion may be derived from inorganic acids, for instance, chloride, bromide, sulphate, iodide nitrate, phosphate, and organic acids, for instance, sulphonates (such as the methanesulphonate and p-toluenesulphonate), acetate, maleate, fumarate, tartrate and formate.

The compounds of the invention are usefully pharmaceutically. In particular they are indicated for use as anti-ulcer agents. The following procedures may be used to test activity.

PROCEDURE A

GASTRIC SECRETION: PYLORUS - LIGATED RAT

Reference: Shay, H; Sun, D. & Gruentstein, M. Gastroenterology 26: 906–913 (1954)
Test Animal: Rat
Procedure:

Male Charles River rats, weighing 180–220 g, are deprived of food overnight, but allowed water. They are housed in separate cages with widemesh grids to avoid coprophagy. Next morning each rat is anaesthetised with halothane, a small mid-line incision is made and the pylorus is ligated. The test compound or vehicle is administered by an appropriate route, usually by injecting a volume of 5 ml/kg into the stomach, or 1 ml/kg into the duodenum. The wound is sutured, and the animal allowed to recover. The operation takes 3–5 minutes. Four hours after pylorus ligation each rat is killed, its stomach is removed and the volume of the gastric contents is measured; the sample is discarded if it contains food or faeces.

Gastric juice is titrated against N NaOH, using a Metrohm automatic titrator. The following variables are evaluated.

1. Concentration of acid.
2. Amount of "free acid", but titrating to pH3.
3. "Total acid", by further titration to pH10.

These variables are expressed in milliequivalents per milliliter. The mean volume of gastric contents, and the three variables above, are expressed as percentage of the corresponding control values.

PROCEDURE B

GASTRIC ULCERS CAUSED BY COLD-RESTRAINT STRESS

Reference: Modification of procedure of Brodie, D. A. and Hanson, H, J.Appl. Physiol. 15:291–294 (1960)
Test Animal: Rat
Object: To detect compounds which will prevent ulcer formation in the glandular portion of the rat stomach.
Procedure:

Male Charles River rats weighing between 120–160 gm. are deprived of food for 18 hr. with water ad lib. The rats are divided into groups of 10 and dosed by the oral route with test compound, 50 mg/kg. or a vehicle control, 0.5% carboxymethylcellulose, in a volume of 5 ml/kg. Immediately after dosing the animals are inserted into aluminium restraining tubes measuring 1⅜ inches in diameter by 8 inches and placed in the cold (4° ± 1° C.). The time in the cold is adjusted so that 90% of the control animals exhibit ulcers. At the end of the test period the animals are killed, the duodenum and esophagus ligated, and the stomach removed. The stomachs are inflated with water, opened along the lesser curvature, spread over the index finger, and the mucosa wiped off to expose the submucosa. The number of hemorrhage sites in the submucosa is counted by visual observation and recorder; however, since these numbers are so variable, only the incidence of ulcer (i.e., the number of rats with ulcers) are used for evaluation.

Compounds are reported by determining a percent inhibition which is calculated as follows:

$$\frac{100 \times \% \text{ rats with ulcers in control} - \% \text{ rats with ulcers in treatment}}{\% \text{ rats with ulcers in control}} = \text{inhibiton}$$

The compounds having formula I and their pharmaceutically acceptable acid addition salts show activity in Procedure A. For instance the products of Examples 1 to 6 and 9 and 10 herein show activity in Procedure A at a dose of 30 milligrams per kilogram i.d. The thiazolothiazinium compounds of the invention show activity in Procedure B. For instance the products of Examples 7 and 8 herein show activity in Procedure B at a dose of 100 milligrams per kilogram p.o.

The invention also includes pharmaceutical compositions containing as active ingredients a compound of formula I, a pharmaceutically acceptable acid addition salt thereof or a thiazolothiazinium compound comprising the cation of formula II and a pharmaceutically acceptable anion. The active ingredient may be micronised, if desired. In addition to the active ingredient, said compositions may also contain a non-toxic carrier. Any suitable carrier known in the art can be used to prepare the pharmaceutical compositions. In such a composition the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient.

In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and exilirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable.

In other instances compositions can be made by dispersing the finely-divided active ingrdient in aqueous starch or sodium carboxymethyl cellulose solution, or in a suitable oil, for instance arachis oil. Liquid pharmaceutical compositions which are sterile or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The invention is illustrated by the following Examples:

EXAMPLE 1

6-Hydroxy-3-methyl-6-phenyl-3,4,6,7-tetrahydro-2H-thiazolo[3,2-a]-s-triazine

A solution of 5.0 grams (0.025 moles) of phenacylbromide in 40 milliliters of acetone was mixed with a solution of 3.27 grams (0.025 moles) of 3,4,5,6-tetrahydro-5-methyl-s-triazin 2(1H)thione in 450 milliliters of acetone. 6-Hydroxy-3-methyl-6-phenyl-3,4,6,7-tetrahydro-2H-thiazolo[3,2-a]-s-triazine hydrobromide crystallized out as a colourless solid, m.p. 149°–150° C. (decomposition). The yield was 7.35 grams (89%).

Analysis. Found = C, 43.2; H, 4.86%; N, 12.6%. $C_{12}H_{16}BrN_3OS$ requires C, 43.6%; H, 4.89%; N, 12.7%.

EXAMPLE 2

6-p-Bromophenyl-6-hydroxy-3-methyl-3,4,6,7-tetrahydro-2H-thiazolo[3,2-a]-s-triazine A solution of 6.95 grams (0.025 moles) of p-bromophenacylbromide in 60 milliliters of acetone was mixed with a solution of 3.27 grams (0.025 moles) of 3,4,5,6-tetrahydro-5-methyl-s-triazin 2(1H) thione in 450 milliliters of acetone. 6-p-Bromophenyl-6-hydroxy-3,4,6,7-tetrahydro-2H-thiazolo[3,2-a-]-s-triazine hydrobromide crystallized out as a colourless solid, m.p. 138°–140° C. (decomposition). The yield was 7.5 grams (75%).

Analysis. Found = 35.5%; H, 3.68%; N, 10.1%. $C_{12}H_{15}Br_2N_3OS$ requires C, 35.2%; H, 3.69%; N, 103%.

EXAMPLE 3

6-p-Bromophenyl-3-ethyl-6-hydroxy-3,4,6,7-tetrahydro-2H-thiazolo[3,2-a]-s-triazine A solution of 6.95 grams (0.025 moles) of p-bromophenacylbromide in 60 milliliters of acetone was mixed with a solution of 3.62 grams (0.025 moles) of 5-ethyl 3,4,5,6-tetrahydro-s-triazin 2(1H) thione in 500 milliliters of acetone. After 10 minutes 6-p-bromophenyl-3-ethyl-6-hydroxy-3,4,6,7-tetrahydro-2H-thiazolo(3,2-a)-s-triazine hydrobromide crystallized out as a colourless solid, m.p. 132°–134° C. The yield was 9.27 grams (88%).

Analysis. Found = C, 37.2%; H, 4.16%; N, 9.93%. $C_{13}H_{17}Br_2N_3OS$ requires C, 36.9%; H, 4.05%; N, 9.93%.

EXAMPLE 4

3-Benzyl-6-hydroxy-6-phenyl-3,4,6,7-tetrahydro-2H-thiazolo-[3,2-a]-s-triazine

A solution of 5.0 grams (0.025 moles) of phenacyl bromide in 40 milliliters of acetone was mixed with a solution of 5.2 grams (0.025 moles) of 5-benzyl-3,4,5,6-tetrahydro-s-triazine-2(1H)-thione in 1200 milliliters of the same solvent and left for 2 hours at room temperature. The solution was then concentrated to 300 milliliters and left overnight. 3-Benzyl-6-hydroxy-6-phenyl-3,4,6,7-tetrahydro-2H-thiazolo[3,2-a]-s-triazine hydrobromide acetonate crystallized as a pale brown solid, m.p. 97°–99° C. The yield was 9.5 grams (82%).

Analysis. Found = C, 54.7%; H, 5.80%; N, 9.24%. $C_{21}H_{26}BrN_3O_2S$ requires C, 54.3%; H, 5.64%; N, 9.04%.

EXAMPLE 5

6-(3,4-Dichlorophenyl)-6-hydroxy-3-methyl-3,4,6,7-tetrahydro-2H-thiazolo-[3,2-a]-s-triazine A solution of 6.7 grams (0.025 mole) of 3,4-dichlorophenacyl bromide in 65 milliliters of acetone was mixed with a solution of 3.27 grams (0.025 mole) of 3,4,5,6-tetrahydro-5-methyl-s-triazin-2(1H-thione in 500 milliliters of acetone. After five minutes, 6-(3,4-dichlorophenyl)-6-hydroxy-3-methyl-3,4,6,7-tetrahydro-2H-thiazolo-[3,2-a]-s-triazine hydrobromide crystallised as the hemiacetonate, melting point 155°–156° C. ( with decomposition). The yield was 8.0 grams (75%).

Analysis. Found: C, 37.8%; H, 4.06; N, 9.80%. $C_{12}H_{14}BrCl_2OS.\frac{1}{2}C_3H_6O$ requires C, 37.9%; H, 4.00%; N, 9.81%.

Example 6

6-(2,4-Dichlorophenyl)-6-hydroxy-3-methyl-3,4,6,7-tetrahydro-2H-thiazolo-[3,2-a]-s-triazine A solution of 6.7 grams (0.025 mole) of 2,4-dichlorophenacyl bromide in 80 milliliters of acetone was mixed with a solution of 3.27 grams (0.025 mole) of 3,4,5,6-tetrahydro-5-methyl-5-triazine-2(1H)-thione in 450 milliliters of acetone. The mixture was left for 30 minutes at room temperature. 7.4 Grams (74% yield) of the title compound as the hydrobromide crystallised as a colourless solid, melting point 153°–155° C. (with decomposition).

Analysis. Found: C, 36.56%; H, 3.60%; N, 10.29%. $C_{12}H_{14}BrCl_2N_3OS$ requires C, 36.11%; H, 3.54%; N, 10.53%.

EXAMPLE 7

6-(p-Bromophenyl)-3-ethyl-6-hydroxy-1-methyl-3,4,6,7-tetrahydro-2H-thiazolo-[3,2-a]-triazinium bromide A solution of 3.7 grams (0.015 mole) of p-bromophenacyl bromide in 30 milliliters of acetone was added to a solution of 2.12 grams (0.015 mole) of 5-ethyl-1-methyl-3,4,5,6-tetrahydro-s-triazine-2(1H)-thione in 100 milliliters of acetone. The mixture was stirred for 4 hours, then allowed to stand. The resulting white precipitate was collected to give 4.52 grams (70% yield) of the title compound, melting point 151°–153° C.

Analysis. Found: C, 38.4%; H, 4.51%; N, 9.50%. $C_{14}H_{19}Br_2N_3OS$ requires C, 38.5%, H, 4.38%; N, 9.62%.

EXAMPLE 8

3-Ethyl-6-hydroxy-1-methyl-6-phenyl-3,4,6,7-tetrahydro-2H-thiazolo-[3,2-a]-triazinium bromide A solution of 3.98 grams (0.02 mole) of phenacyl bromide in 30 milliliters of acetone was added to a solution of 3.18 grams (0.02 mole) of 5-ethyl-1-methyl-3,4,5,6-tetrahydro-s-triazine-2(1H)-thione in 150 milliliters of acetone. The mixture was stirred for 30 minutes and then allowed to stand. The resulting white precipitate was collected to give 5.7 grams (80% yield) of the title compound, melting point 135°–137° C.

Analysis. Found: C, 47.1%; H, 5.65%; N, 11.4%. $C_{14}H_{20}N_3OSBr$ requires C, 46.9%; H, 5.63%; N, 11.7%.

EXAMPLE 9

3-Allyl-6-(p-bromophenyl)-6-hydroxy-3,4,6,7-tetrahydro-2H-thiazole [3,2-a]-s-triazine A solution of 6.95 grams (0.025 mole) of p-bromophenacyl bromide in 60 milliliters of acetone was mixed with a solution of 3.93 grams (0.025 mole) 5-allyl-3,4,5,6-tetrahydro-s-triazin-2(1H)-thione in 1100 milliliters of acetone and the mixture was left for 1 hour at room temperature. The solution was then concentrated to 200 milliliters. 10.1 Grams (89% yield) of 3-allyl-6-(p-bromophenyl)-6-hydroxy-3,4,6,7-tetrahydro-2H-thiazolo[3,2-a]-s-triazine hydrobromide ⅓ acetonate crystallised as a colourless solid of melting point 146°–148° C. (with decomposition).

Analysis. Found: C, 39.5%; H, 4.02%; N, 9.34%. $C_{14}H_{17}Br_2N_3OS.\frac{1}{3}C_3H_6O$ requires C, 39.6%; H, 4.21%; N, 9.24%.

EXAMPLE 10

3-Allyl-6-hydroxy-6-phenyl-3,4,6,7-tetrahydro-2H-thiazolo [3,2-a]-s-triazine

A solution of 5.0 grams (0.025 mole) of phenacyl bromide in 40 milliliters of acetone was mixed with a solution of 3.93 grams (0.025 mole) of 5-allyl-3,4,5,6-tetrahydro-s-triazin-2(1H)-thione in 1100 milliliters of acetone and the mixture was left for 1 hour at room temperature. The solution was concentrated to 100 milliliters and left overnight. 8.1 Grams (86% yield) of 3-allyl-6-hydroxy-6-phenyl-3,4,6,7-tetrahydro-2H-thiazolo[3,2-a]-s-triazine hydrobromide ⅓ acetonate crystallised out as a colourless solid, melting point 118°–120° C.

Analysis. Found: C, 48.3%; H, 5.36%; N, 11.5%. $C_{14}H_{18}BrN_3OS.\frac{1}{3}C_3H_6O$ requires C, 48.0%; H, 5.37%; N, 11.2%.

EXAMPLE 11

In a similar manner to the preceeding Examples, the following reactants are reacted with 3,4,5,6-tetrahydro-5-methyl-s-triazin-2(1H)-thione to give the following products as hydrobromides:

| REACTANT | PRODUCT |
| --- | --- |
| 1. m-Methoxyphenacyl bromide | 6-Hydroxy-6-(m-methoxyphenyl)-3-methyl-3,4,6,7-tetrahydro-2H-thiazolo-[3,2-a]-s-triazine |
| 2. p-Nitrophenacyl bromide | 6-Hydroxy-3-methyl-6-(p-nitrophenyl)-3,4,6,7-tetrahydro-2H-thiazolo-[3,2-a]-s-triazine |
| 3. p-Dimethylaminophenacyl bromide | 6-(p-Dimethylaminophenyl)-6-hydroxy-3-methyl-3,4,6,7-tetrahydro-2H-thiazolo-[3,2-a]-s-triazine |
| 4. m-Trifluoromethylphenacyl bromide | 6-Hydroxy-3-methyl-6-(m-trifluoromethylphenyl)-3,4,6,7-tetrahydro-2H-thiazolo-[3,2-a]-s-triazine |
| 5. p-Methylphenacyl bromide | 6-Hydroxy-3-methyl-6-(p-methylphenyl)-3,4,6,7-tetrahydro-2H-thiazolo-[3,2-a]-s-triazine |
| 6. m-Aminophenacyl bromide | 6-(m-Aminophenyl)-6-hydroxy-3-methyl-3,4,6,7-tetrahydro-2H-thiazolo-[3,2-a]-s-triazine. |
| 7. p-Methylaminophenyl bromide | 6-Hydroxy-3-methyl-6-(p-methylaminophenyl)-3,4,6,7-tetrahydro-2H-thiazolo-[3,2-a]-s-triazine |

EXAMPLE 12

In a similar manner to the preceeding Examples, phenacyl bromide is reacted with 1-benzyl-5-ethyl-3,4,5,6-tetrahydro-s-triazin-2(1H)-thione and 1-allyl-5-ethyl-3,4,5,6-tetrahydro-s-triazin-2(1H)-thione to give, respectively, 1-benzyl-3-ethyl-6-hydroxy-6-phenyl-3,4,6,7-tetrahydro-2H-thiazolo-[3,2-a]-triazinium bromide and 1-allyl-3-ethyl-6hydroxy-6-phenyl-3,4,6,7-tetrahydro-2H-thiazolo-[3,2-a]-triazinium bromide.

What is claimed is:

1. A compound selected from those having the formula

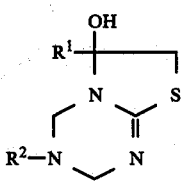

their pharmaceutically acceptable acid addition salts and their derivatives comprising a cation having the formula

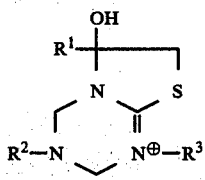

and a pharmaceutically acceptable anion, wherein $R^1$ is selected from phenyl and phenyl substituted by one to two substituents selected from halogen, trifluoromethyl, lower alkoxy, lower alkyl, nitro, amino, mono(-lower alkyl)amino and di(lower alkyl)amino; $R^2$ is selected from phen(lower)alkyl, lower alkyl and lower alkenyl and, where present, $R^3$ is selected from phen(-lower)alkyl, lower alkyl and lower alkenyl.

2. A compound as claimed in claim 1, which is 6-hydroxy-3-methyl-6-phenyl-3,4,6,7-tetrahydro-2H-thiazolo-[3,2-a]-s-triazine or a pharmaceutically acceptable acid addition salt thereof.

3. A compound as claimed in claim 1, which is 6-(p-bromophenyl)-6-hydroxy-3-methyl-3,4,6,7-tetrahydro-2H-thiazolo-[3,2-a]-s-triazine or a pharmaceutically acceptable acid addition salt thereof.

4. A compound as claimed in claim 1, which is 6-(p-bromophenyl)-3-ethyl-6-hydroxy-3,4,6,7-tetrahydro-2H-thiazolo-[3,2-a]-s-triazine or a pharmaceutically acceptable acid addition salt thereof.

5. A compound as claimed in claim 1, which is 3-benzyl-6-hydroxy-3-phenyl-3,4,6,7-tetrahydro-2H-thiazolo-[3,2-a]-s-triazine or a pharmaceutically acceptable acid addition salt thereof.

6. A compound as claimed in claim 1, which is 6-(3,4-dichlorophenyl)-6-hydroxy-3-methyl-3,4,6,7-tetrahydro-2H-thiazolo-[3,2-a]-s-triazine or a pharmaceutically acceptable acid addition salt thereof.

7. A compound as claimed in claim 1, which is 6-(2,4-dichlorophenyl-6-hydroxy-3-methyl-3,4,6,7-tetrahydro-2H-thiazolo-[3,2-a]-s-triazine or a pharmaceutically acceptable acid addition salt thereof.

8. A compound as claimed in claim 1, which is 3-allyl-6-(p-bromophenyl)-6-hydroxy-3,4,6,7-tetrahydro-2H-thiazolo-[3,2-a]-s-triazine or a pharmaceutically acceptable acid addition salt thereof.

9. A compound as claimed in claim 1, which is 3-allyl-6-hydroxy-6-phenyl-3,4,6,7-tetrahydro-2H-thiazolo-[3,2-a]-s-triazine or a pharmaceutically acceptable acid addition salt thereof.

10. A compound as claimed in claim 1, which is 3-ethyl-6-hydroxy-1-methyl-6-phenyl-3,4,6,7-tetrahydro-2H-thiazolo-[3,2-a]-triazinium bromide.

11. A compound as claimed in claim 1, which is 6-(p-bromophenyl)-3-ethyl-6-hydroxy-1-methyl-3,4,6,7-tetrahydro-2H-thiazolo-[3,2-a]-triazinium bromide.

12. A pharmaceutical composition useful as an anti-ulcer agent, comprising an effective amount of a compound as claimed in claim 1 in association with a pharmaceutically suitable non-toxic carrier.

* * * * *